United States Patent [19]

Biedermann et al.

[11] Patent Number: 4,482,474

[45] Date of Patent: Nov. 13, 1984

[54] PHOSPHOLIPID SOLUTIONS

[75] Inventors: Juergen Biedermann, Pulheim-Stommeln; Hans Betzing, Kerpen-Horrem, both of Fed. Rep. of Germany

[73] Assignee: A. Nattermann & Cie GMBH, Cologne, Fed. Rep. of Germany

[21] Appl. No.: 493,672

[22] Filed: May 11, 1983

[30] Foreign Application Priority Data

May 13, 1982 [DE] Fed. Rep. of Germany ....... 3218027

[51] Int. Cl.$^3$ ...................... B01J 13/00; A61K 31/66; A23J 7/02
[52] U.S. Cl. .................................. 252/311; 424/199; 426/662; 252/357
[58] Field of Search .................. 252/311; 424/199, 38; 426/662

[56] References Cited

U.S. PATENT DOCUMENTS 3,966,918  6/1976  Kawamata et al. ................. 424/182
4,140,759  2/1979  Mausner ............................... 424/70

OTHER PUBLICATIONS

World Soybean Res. Conf., B. F. Szukaj, 11 1979—Westview Press, pp. 681–691.
J. Am. Soc. 59, G. F. D'Alelio and E. Emmet Reid, 111–112 (1937).

*Primary Examiner*—Richard D. Lovering
*Assistant Examiner*—Anne Brookes
*Attorney, Agent, or Firm*—Pearne, Gordon, Sessions, McCoy, Granger & Tilberry

[57] ABSTRACT

Aqueous phospholipid solutions and their preparations, consisting of phospholipids and a solution promoter of the general formula $CH_3(CH_2)_nCONHCH_2CH_2OH$, in which n is 3, 4 or 5.

18 Claims, No Drawings

PHOSPHOLIPID SOLUTIONS

The present invention relates to aqueous phospholipid solutions and their preparation according to claims 1–18.

Phospholipids are natural or synthetic products. They have numerous uses in the food and pharmaceutical industries and in technology generally (B F Szukaj in World Soybean Res. Conf. II 1979—Westview Press, pp 681–91).

As a rule, phospholipids are plastic substances the working of which presents technical difficulties, and which are soluble in organic solvents such as hexane, or in mineral oil and the like, but insoluble in water. For many of their applications, however, organic solvents are undesired. Thus because of their insolubility in water, emulsions have to be prepared, and these are often insufficiently stable or subject to limitations in use. It is therefore desirable to have clear aqueous solutions of phospholipids which, in use, are easy to introduce into the most varied products.

It has now been found, surprisingly, that hydroxyethyl amides of the general Formula I

   I in which n is 3,4 or 5, when used as solution promoters, result in clear aqueous phospholipid solutions. The solutions obtained have a neutral pH and are stable even on prolonged storage.

Suitable hydroxyethyl amides are:

N-(2-Hydroxethyl) valeric acid amide
N-(2-Hydroxyethyl) caproic acid amide
N-(2-Hydroxyethyl) heptanoic acid amide With regard to the phospholipids, all natural and synthetic phospholipids can be used.

Specially suitable natural phospholipids are Phosphatidyl choline, Phosphatidyl ethanolamine, Phosphatidyl inositol, Lysophosphatidyl choline, N-acyl phosphatidyl ethanolamine and Phosphatidic acid, as well as mixtures of these phospholipids.

Examples of mixtures of phospholipids are:

(A)

Phosphatidyl chloline: 50.1%
Phosphatidyl ethanolamine: 23.7%
Lysophosphatidyl choline: 1.7%
Phosphatidyl inositol: 6.1%
N-acyl phosphatidyl ethanolamine: 5.2%
Phosphatidic acid: 2.1%
Glycolipids and triglycerides: 11.2%

(B)

Phosphatidyl choline 11.4%
Phosphatidyl ethanolamine 27.4%
Lysophosphatidyl choline 1.3%
Phosphatidyl inositol 27.0%
N-acyl phosphatidyl ethanolamine 1.2%
Phosphatidic acid 15.0%
Glycolipids and triglycerides 16.5%

(C)

Phosphatidyl choline 26.2%
Phosphatidyl ethanolamine 25.1%
Lysophosphatidyl choline 1.3%
Phosphatidyl inositol 21.4%
N-acyl phosphatidyl ethanolamine 5.3%
Phosphatidic acid 12.6%
Glycolipids and triglycerides 7.8%

The surprising solution promoting power of the non-ionic fatty acid-N-(2-hydroxyethyl)-amides for phospholipids rises in the holmologous series with increasing chain length of the fatty acids: $C_5<C_6<C_7$. The expected reduction of the amount necessary for solubilisation in proceeding to the $C_8$-acid (octanoic acid) cannot in practice be exploited, since the hydroxyethyl amide of octanoic acid is insoluble in water.

The minimum amount of solubiliser necessary for the most complete water solubility of the phospholipid is dependent on the chain length of the hydroxyethyl amide used. While 1.5 parts of N-(2-Hydroxyethyl) valeric acid amide are necessary for one part of phospholipid, a mere 1.2 parts of N-(2-Hydroxyethyl) caproic acid amide is sufficient for one part of phospholipid, and complete water solubility of the phospholipid is achieved with only 0.75 parts of N-(2-Hydroxyethyl) heptanoic acid amide.

The concentrations of the phospholipids in the solution can be varied inside broad limits by the use of these pH-neutral nonionic solubilisers, which make possible solutions with a content of 1–25% phospholipid, preferably a content of 5–10% phospholipid.

The hydroxyethyl amides necessary for the preparation of the phospholipid solutions according to the invention were obtained as prescribed by G F D'Alelio and E Emmet Reid, J. Am. Soc. 59, 111–112 (1937). The preparation of the aqueous phospholipid solutions according to the invention is carried out by first dissolving the relevant hydroxyethyl amide at 20° C. in about one tenth of the amount of water necessary for the desired final concentration of the phospholipid solution. Then the phospholipid is added and the mixture stirred at 20° C. until a clear solution of oily consistency is obtained. The remainder of the water is added slowly with further stirring until a clear phospholipid solution which has a pH value around the neutral point and is stable at room temperature is obtained.

The preparation of the phospholipid solutions according to the invention is described in more detail by the following examples.

EXAMPLE 1

7.5 g N-(2-Hydroxethyl) valeric acid amide is dissolved in 10 ml water at 20° C. After addition of 5 g phospholipid of the following composition:

Phosphatidyl choline: 96%
Lysophosphatidyl choline max.: 3%
Triglycerides max.: 1% the mixture is stirred at 20° C. until such time as a clear solution of oil consistency has appeared. 77.5 ml water is then added slowly with further stirring, and there is obtained a clear, stable phospholipid solution which has a pH value about the neutral point.

EXAMPLE 2

12 g N-(2-Hydroxyethyl) caproic acid amide is dissolved in 10 ml water at 20° C. After addition of 10 g phospholipid having the composition given in Example 1, stirring is continued at 20° C. until a clear solution of oily consistency has appeared. 68 ml water is then added slowly with further stirring, and there is obtained a clear stable phospholipid solution which has a pH value about the neutral point.

EXAMPLE 3

15 g N-(2-Hydroxyethyl) heptanoic acid amide is dissolved in 10 ml water at 20° C. After addition of 20 g phospholipid having the composition given in Example 1, stirring is continued at 20° C. until a clear solution of oily consistency has appeared. 65 ml water is then added slowly with further stirring, and there is obtained a clear stable phospholipid solution, which has a pH value about the neutral point.

EXAMPLE 4

4.5 g N-(2-Hydroxyethyl) heptanoic acid amide is dissolved in 10 ml water at 20° C. After addition of 6 g phospholipid of the following composition
Phosphatidyl choline 50.1%
Phosphatidyl ethanolamine 23.7%
Lysophosphatidyl choline 1.7%
Phosphatidyl inositol 6.1%
N-acyl phosphatidyl ethanolamine 5.2%
Phosphatidic acid 2.1%
Glycolipids and triglycerides 11.2%
stirring is continued at 20° C. until a clear solution of oily consistency has appeared. 79.5 ml water is then added slowly with further stirring, and there is obtained a clear stable phospholipid solution, which has a pH value about the neutral point.

EXAMPLE 5

12 g N-(2-Hydroxethyl) caproic amide is dissolved in 10 ml water at 20° C. After addition of 10 g phospholipid having the composition given in Example 4, stirring is continued at 20° C. until a clear solution of oily consistency has appeared. 68 ml water is then added slowly with further stirring, and there is obtained a clear stable phospholipid solution, which has a pH value about the neutral point.

EXAMPLE 6

12 g N-(2-Hydroxyethyl) heptanoic acid amide is dissolved in 10 ml water at 20° C. After addition of 16 g phospholipid having the composition given in Example 4, stirring is continued at 20° C. until a clear solution of oily consistency has appeared. 62 ml water is then added slowly with further stirring, and there is obtained a clear stable phospholipid solution, which has a pH value about the neutral point.

EXAMPLE 7

1.5 g N-(2-Hydroxyethyl) heptanoic acid amide is dissolved in 10 ml water at 20° C. After addition of 2 g phospholipid of the following composition
Phosphatidyl choline 11.4%
Phosphatidyl ethanolamine 27.4%
Lysophosphatidyl choline 1.3%
Phosphatidyl inositol 27.0%
N-acyl phosphatidyl ethanolamine 1.2%
Phosphatidic acid 15.0%
Glycolipids and triglycerides 16.5%
stirring is continued at 20° C. until a clear solution of oily consistency has appeared. 86.5 ml water is added slowly with further stirring, and there is obtained a clear stable phospholipid solution, which has a pH value about the neutral point.

EXAMPLE 8

9.6 g N-(2-Hydroxyethyl) caproic acid amide is dissolved in 10 ml water at 20° C. After addition of 8 g phospholipid having the composition given in Example 7 stirring is continued at 20° C. until a clear solution of oily consistency has appeared. 72.4 ml water is then added slowly with further stirring, and there is obtained a clear stable phospholipid solution, which has a pH value about the neutral point.

EXAMPLE 9

12 g N-(2-Hydroxyethyl) heptanoic acid amide is dissolved in 10 ml water at 20° C. After addition of 16 g phospholipid having the composition given in Example 7, stirring is continued at 20° C. until a clear solution of oily consistency has appeared. 62 ml water is then added slowly with further stirring, and there is obtained a clear stable phospholipid solution, which has a pH value about the neutral point.

EXAMPLE 10

6 g N-(2-Hydroxyethyl) valeric acid amide is dissolved in 10 ml water at 20° C. After addition of 4 g phospholipid of the following composition.
Phosphatidyl choline 26.2%
Phosphatidyl ethanolamine 25.1%
Lysophosphatidyl choline 1.3%
Phosphatidyl inositol 21.4%
N-acyl phosphatidyl ethanolamine 5.3%
Phosphatidic acid 12.6%
Glycolipids and triglycerides 7.8%
stirring is continued at 20° C. until a clear solution of oily consistency has appeared. 80 ml water is then added slowly with further stirring, and there is obtained a clear stable phospholipid solution, which has a pH value about the neutral point.

EXAMPLE 11

9.6 g N-(2-Hydroxyethyl) caproic acid amide is dissolved in 10 ml water at 20° C. After addition of 8 g phospholipid having the composition given in Example 10, stirring is continued at 20° C. until a clear solution of oily consistency has appeared. 72.4 ml water is then added slowly with further stirring, and there is obtained a clear stable phospholipid solution, which has a pH value about the neutral point.

EXAMPLE 12

14.4 g N-(2-Hydroxyethyl) caproic acid amide is dissolved in 10 ml water at 20° C. After addition of 12 g phospholipid having the composition given in Example 10, stirring is continued at 20° C. until a clear solution of oily consistency has appeared. 63.6 ml water is then added slowly with further stirring, and there is obtained a clear stable phospholipid solution, which has a pH value about the neutral point.

We claim:
1. Aqueous phospholipid solution comprising as solution promoter a hydroxyethyl amide of the general Formula I

$$CH_3(CH_2)_nCONH-CH_2-CH_2-OH \qquad I$$

in which n is 3, 4 or 5.

2. Aqueous phospholipid solution according to claim 1, wherein the solution contains phosphatidylcholine as the phospholipid.

3. Aqueous phospholipid solution according to claim 1, wherein the solution contains 1–25 parts phospholipid and 0.75–37.5 parts of a hydroxyethyl amide of the Formula I.

4. Aqueous phospholipid solution according to claim 3, wherein the solution contains phosphatidylcholine as the phospholipid.

5. Aqueous phospholipid solution according to claim 1, wherein the solution contains N-(2-Hydroxyethyl)-valeric acid amide as the hydroxyethyl amide.

6. Aqueous phospholipid solution according to claim 5, wherein the solution contains phosphatidylcholine as the phospholipid.

7. Aqueous phospholipid solution according to claim 1, wherein the solution contains N-(2-Hydroxyethyl)-caproic acid amide as the hydroxyethyl amide.

8. Aqueous phospholipid solution according to claim 7, wherein the solution contains phosphatidylcholine as the phospholipid.

9. Aqueous phospholipid solution according to claim 1, wherein the solution contains N-(2-Hydroxyethyl)-heptanoic acid amide as the hydroxyethyl amide.

10. Aqueous phospholipid solution according to claim 9, wherein the solution contains phosphatidylcholine as the phospholipid.

11. Process for the preparation of an aqueous phospholipid solution containing 1 to 25 parts of a phospholipid comprising dissolving the phospholipid in water in the presence of a solution promotor of the general Formula I $$CH_3(CH_2)_n CONHCH_2CH_2OH$$

in which n is 3, 4 or 5.

12. Process according to claim 11, wherein the solution promoter is N-(2-hydroxyethyl)-valeric acid amide, and at least 1.5 parts of the solution promoter are added per each part of phospholipid.

13. Process according to claim 12, wherein the solution contains phosphatidylcholine as a phospholipid.

14. Process according to claim 11, wherein the solution promoter is N-(2-hydroxyethyl)-caproic acid amide, and at least 1.2 parts of the solution promoter is added per each part of the phospholipid.

15. Process according to claim 14, wherein the solution contains phosphatidylcholine as a phospholipid.

16. Process according to claim 11, wherein the solution promotor is N-(2-hydroxyethyl)-heptanoic acid amide, and at least 0.75 parts of the solution promoter is added per each part of the phospholipid.

17. Process according to claim 16, wherein the solution contains phosphatidylcholine as a phospholipid.

18. Process according to claim 11, wherein the solution contains phosphatidylcholine as a phospholipid.

* * * * *

UNITED STATES PATENT AND TRADEMARK OFFICE
CERTIFICATE OF CORRECTION

PATENT NO. : 4,482,474
DATED : November 13, 1984
INVENTOR(S) : Juergen Biedermann et al.

It is certified that error appears in the above—identified patent and that said Letters Patent is hereby corrected as shown below:

Column 1, line 26, Formula I should read as follows:

$$-- CH_3-(CH_2)_n-CONHCH_2-CH_2OH --.$$

Signed and Sealed this

Twenty-seventh Day of August 1985

[SEAL]

Attest:

DONALD J. QUIGG

Attesting Officer  Acting Commissioner of Patents and Trademarks